United States Patent
Ito et al.

(10) Patent No.: US 9,918,938 B2
(45) Date of Patent: Mar. 20, 2018

(54) SELECTIVE PRODUCTION METHOD FOR D-MANNITOL α-FORM CRYSTAL USING SPRAY-DRYING METHOD

(71) Applicant: DAIICHI SANKYO COMPANY, LIMITED, Tokyo (JP)

(72) Inventors: Atsutoshi Ito, Tokyo (JP); Shuichi Yada, Tokyo (JP); Mitsuhide Tanimoto, Tokyo (JP); Michiko Kumon, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 15/024,622

(22) PCT Filed: Sep. 29, 2014

(86) PCT No.: PCT/JP2014/075815
§ 371 (c)(1),
(2) Date: Mar. 24, 2016

(87) PCT Pub. No.: WO2015/046489
PCT Pub. Date: Apr. 2, 2015

(65) Prior Publication Data
US 2016/0228370 A1    Aug. 11, 2016

(30) Foreign Application Priority Data

Sep. 30, 2013 (JP) ................................ 2013-202857

(51) Int. Cl.
*A61K 9/16* (2006.01)
*C07C 29/78* (2006.01)
*C07C 29/76* (2006.01)

(52) U.S. Cl.
CPC .......... *A61K 9/1623* (2013.01); *A61K 9/1635* (2013.01); *A61K 9/1641* (2013.01); *A61K 9/1682* (2013.01); *C07C 29/76* (2013.01); *C07C 29/78* (2013.01)

(58) Field of Classification Search
None
See application file for complete search history.

(56) References Cited

U.S. PATENT DOCUMENTS

2005/0008693 A1   1/2005  Erdmann et al.
2008/0275082 A1  11/2008  Brum et al.

FOREIGN PATENT DOCUMENTS

| CA | 2448814 A1 * | 1/2003 | .......... A61K 9/0019 |
|----|----|----|----|
| EP | 1413310 A1 | 4/2004 | |
| JP | 2005-513151 A | 5/2005 | |
| JP | 2009-510099 A | 3/2009 | |
| WO | WO 2012051426 A2 * | 4/2012 | .......... A61K 9/0075 |
| WO | 2012094381 A2 | 7/2012 | |
| WO | 2012094381 A3 | 7/2012 | |

OTHER PUBLICATIONS

Costantino, Henry R., et al., "Effect of Mannitol Crystallization on the Stability and Aerosol Performance of a Spray-Dried Pharmaceutical Protein, Recombinant Humanized Anti-IgE Monoclonal Antibody", Journal of Pharmaceutical Sciences, vol. 87, No. 11, Nov. 1998, pp. 1406-1411.
Burger, Artur, et al., "Energy/Temperature Diagram and Compression Behavior of the Polymorphs of D-Mannitol", Journal of Pharmaceutical Sciences, vol. 89, No. 4, Apr. 2000, pp. 457-468.
Lee, Yan-Ying, et al., "Particle Size Dependence of Polymorphism in Spray-Dried Mannitol", European Journal of Pharmaceutical Sciences 44 (2011), pp. 41-48.
Littringer, Eva Maria, et al., "Spray Drying of Mannitol as a Drug Carrier—The Impact of Process Parameters on Product Properties", Drying Technology: An International Journal, 30:1, 114-124, DOI: 10.1080/07373937.2011.620726, (2011).
The Pharmaceutical Society of Japan, "Explanations of Pharmaceutical Terminology", "Spray-Drying Method", (2007).
The Pharmaceutical Society of Japan, "Explanations of Pharmaceutical Terminology", "Powder Inhaler.", (2007).
Supplementary European Search Report issued to EP application No. EP 14849690.4, dated Apr. 6, 2017.
Ritsuo Hosokawa, The Ministry of Health, Labour and Welfare Ministerial Notification No. 65, "General Rules for Preparations / Monographs for Preparations," Japanese Pharmacopia XVI, pp. 14-15 (Mar. 24, 2011).
Office Action for Application No. 2015-539411 dated Dec. 13, 2017 in Japanese; and Machine Translation of Office Action dated Dec. 13, 2017 in English.

* cited by examiner

*Primary Examiner* — Deepak R Rao
*Assistant Examiner* — Laura M Daniel
(74) *Attorney, Agent, or Firm* — Locke Lord LLP

(57) ABSTRACT

An object of the present invention is to provide a method for producing selectively a powder particle consisting of the α-form crystal of D-mannitol, using the spray-drying method. It is a method for selective production of powder particles consisting of the α-form crystal of D-mannitol, wherein a D-mannitol solution containing a water-soluble polymer is spray-dried.

9 Claims, 22 Drawing Sheets

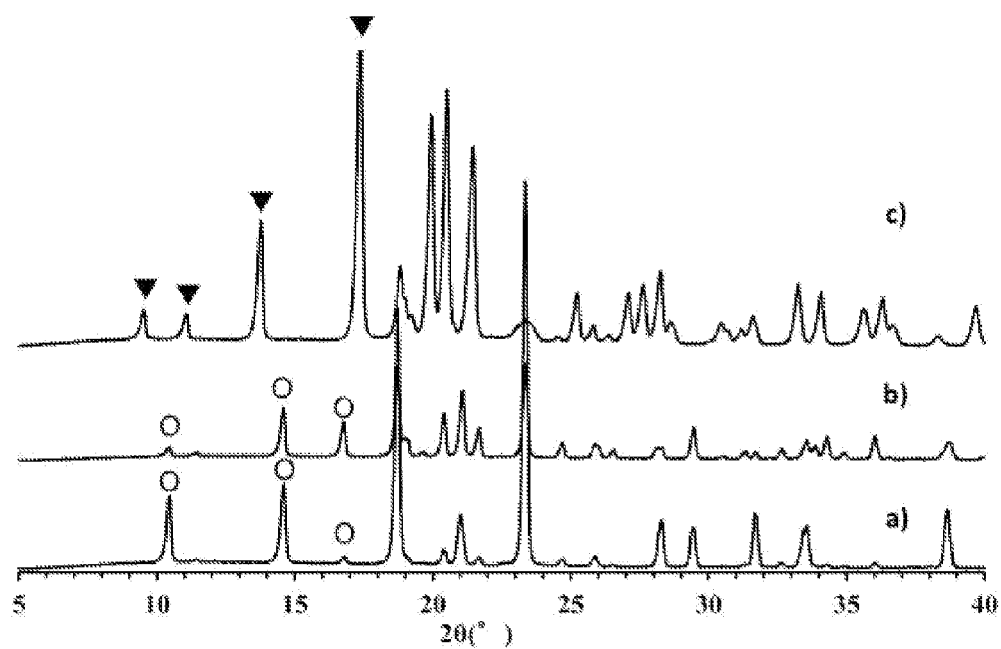
[Fig. 1]

[Fig. 2]
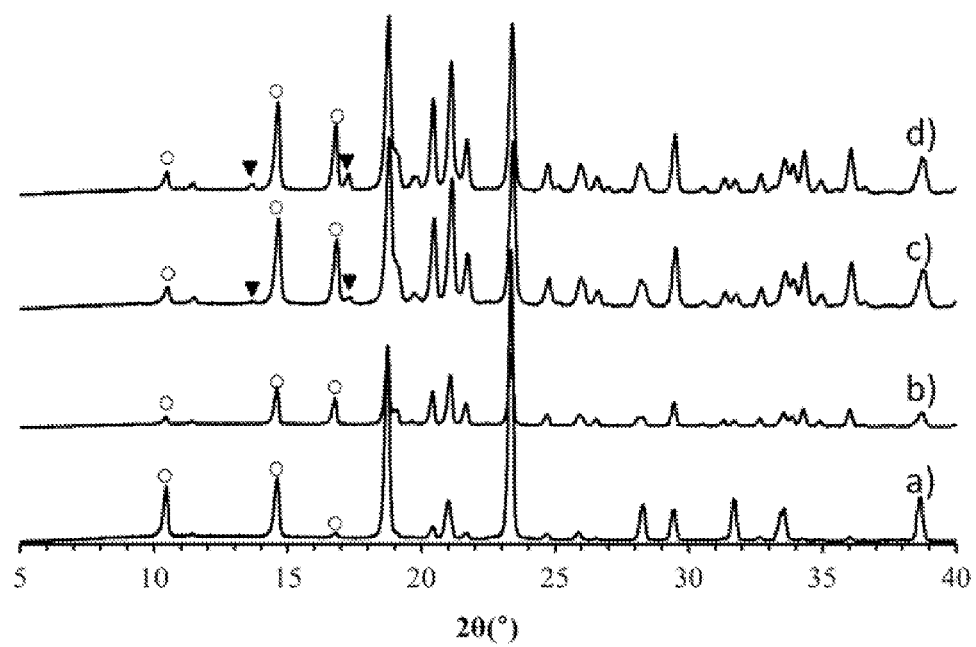

[Fig. 3]
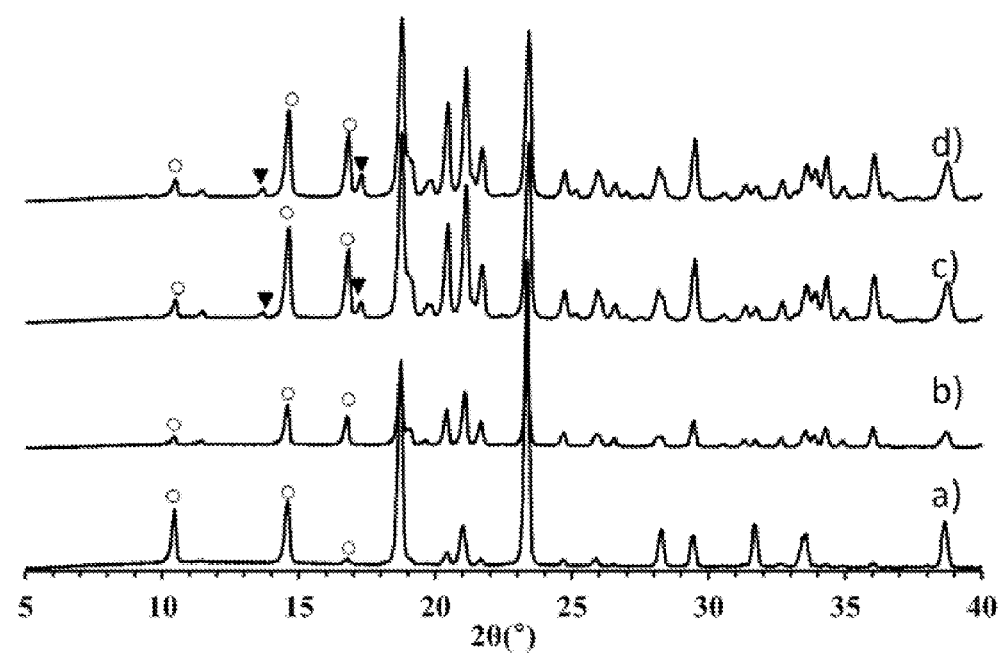

[Fig. 4]
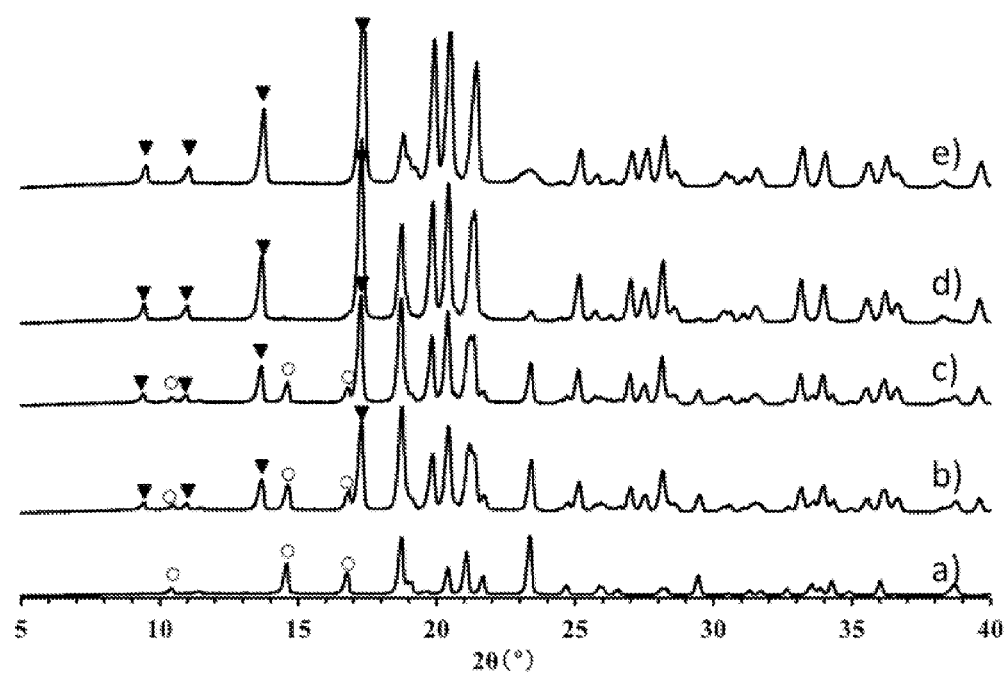

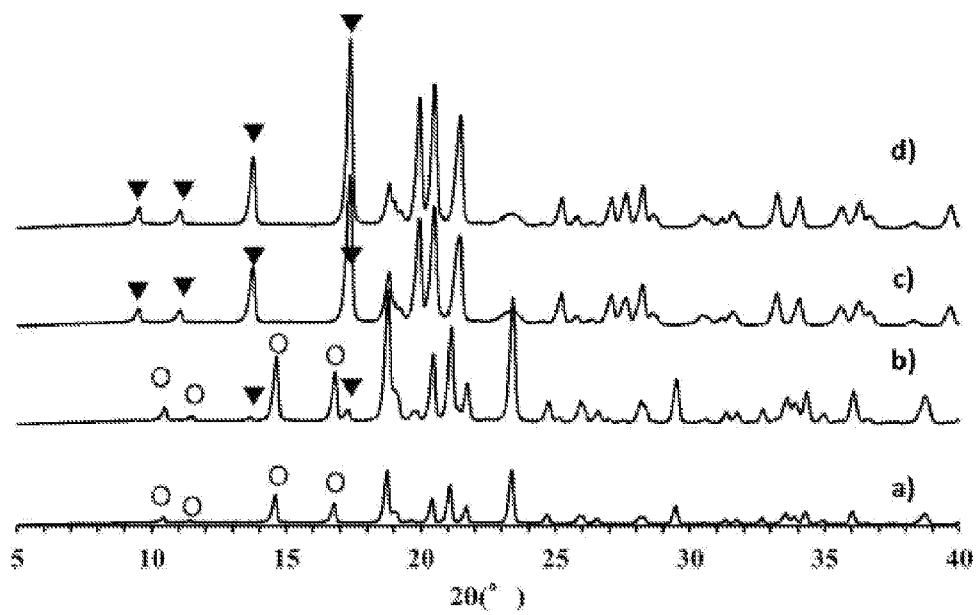
[Fig. 5]

[Fig. 6]
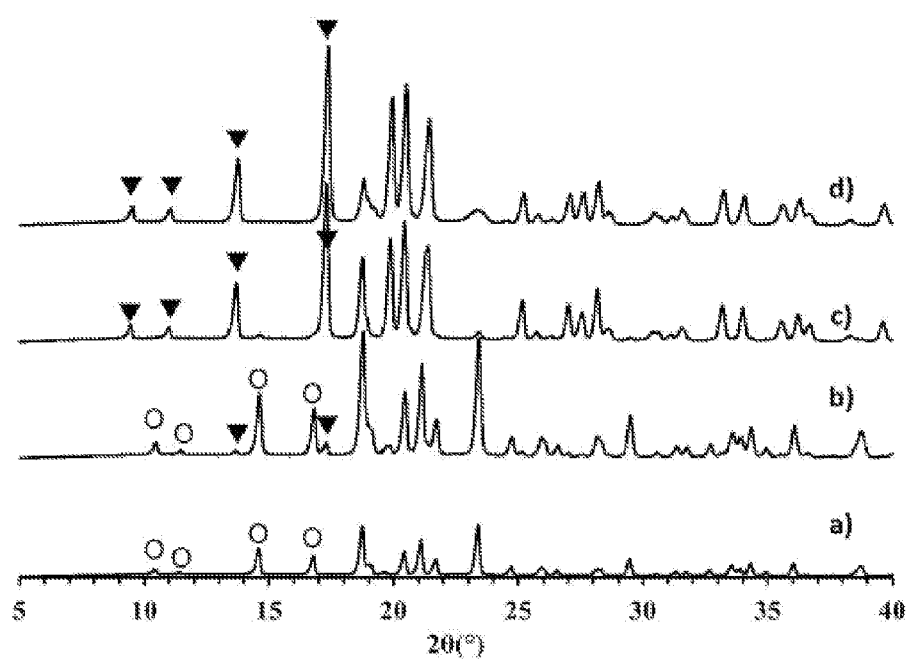

[Fig. 7]
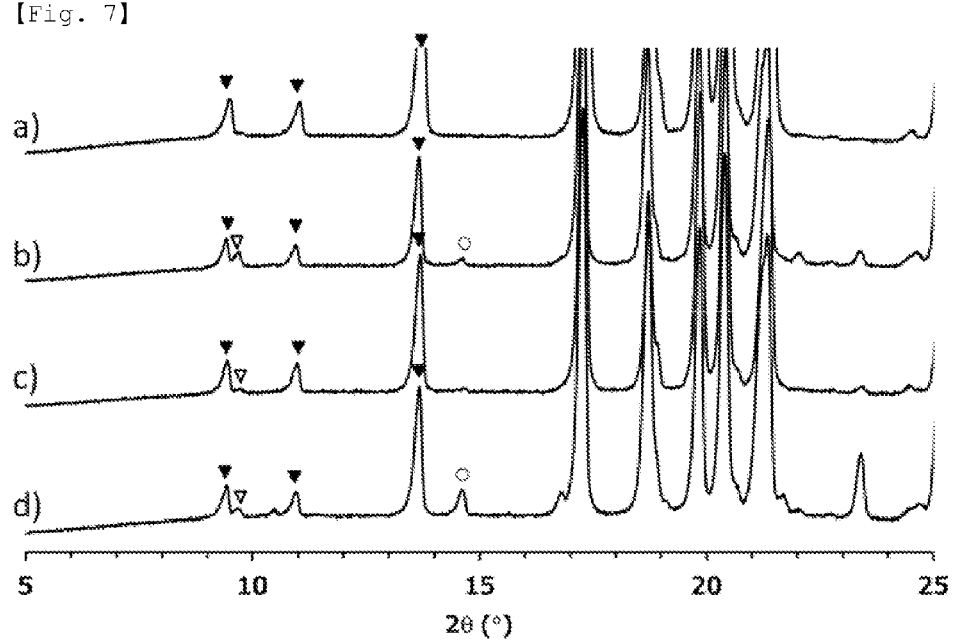

[Fig. 8]
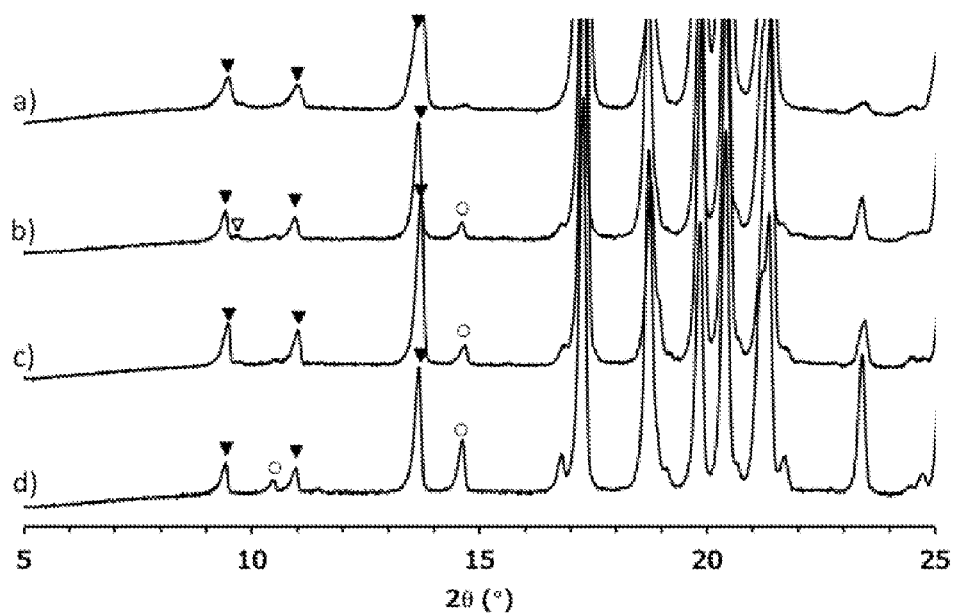

[Fig. 9]
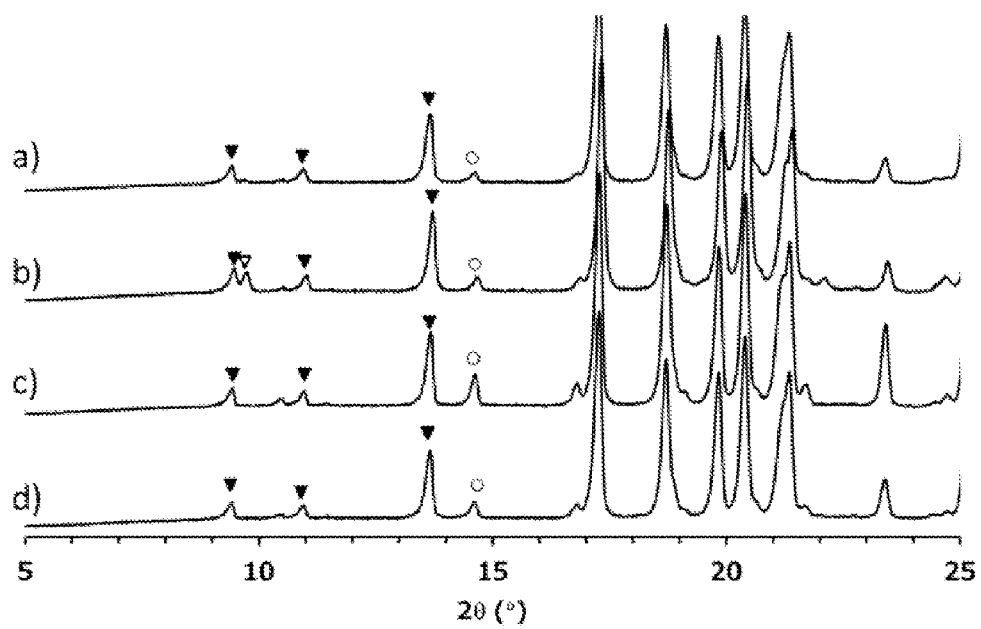

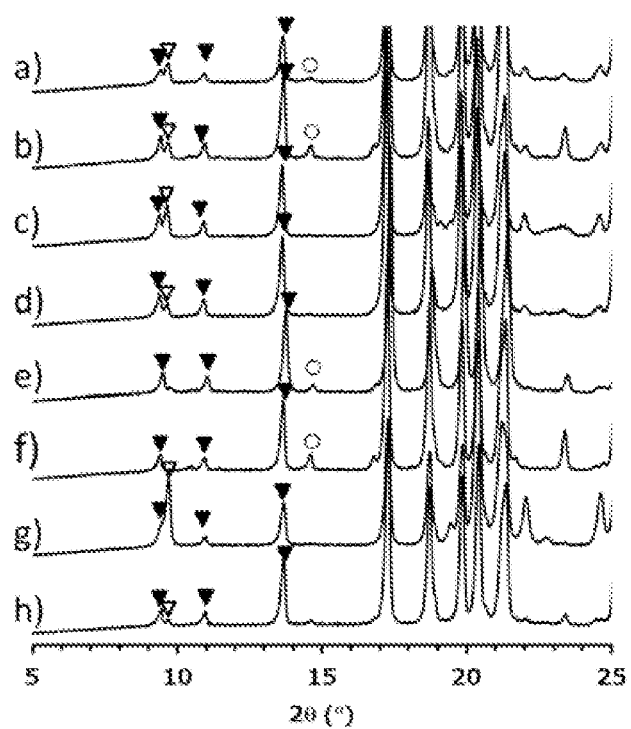
[Fig. 10]

[Fig. 11]
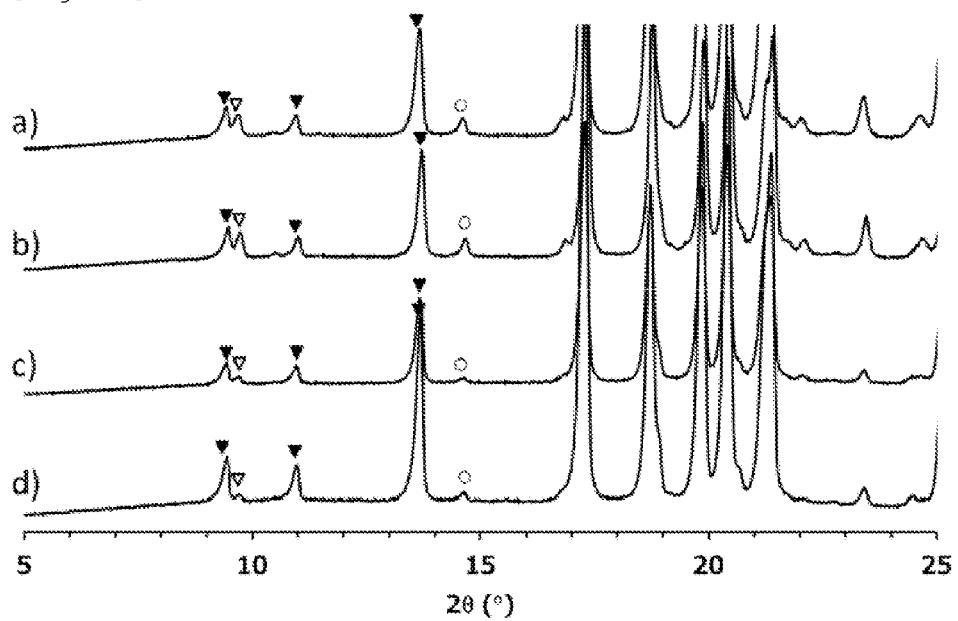

[Fig. 12]
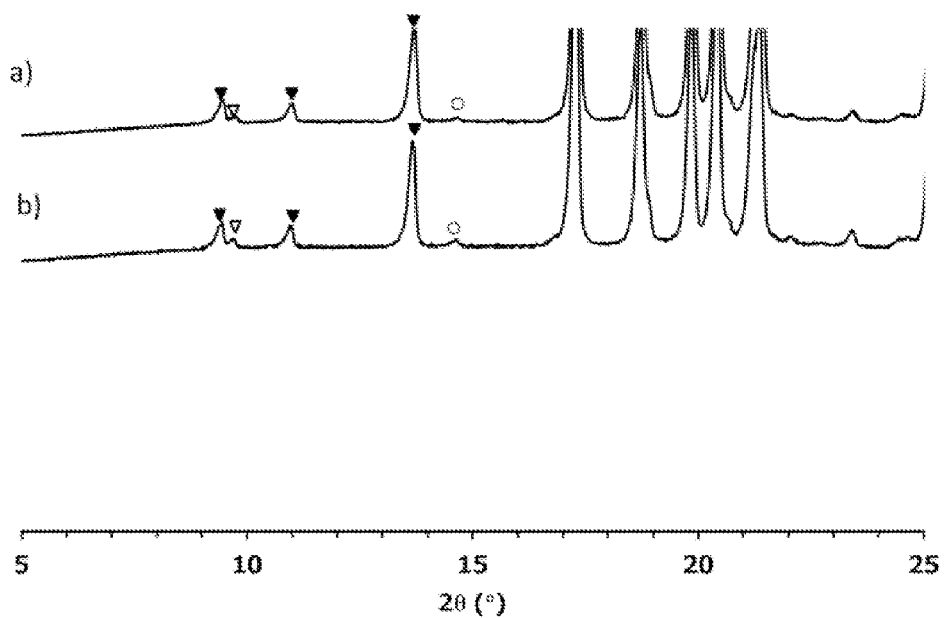

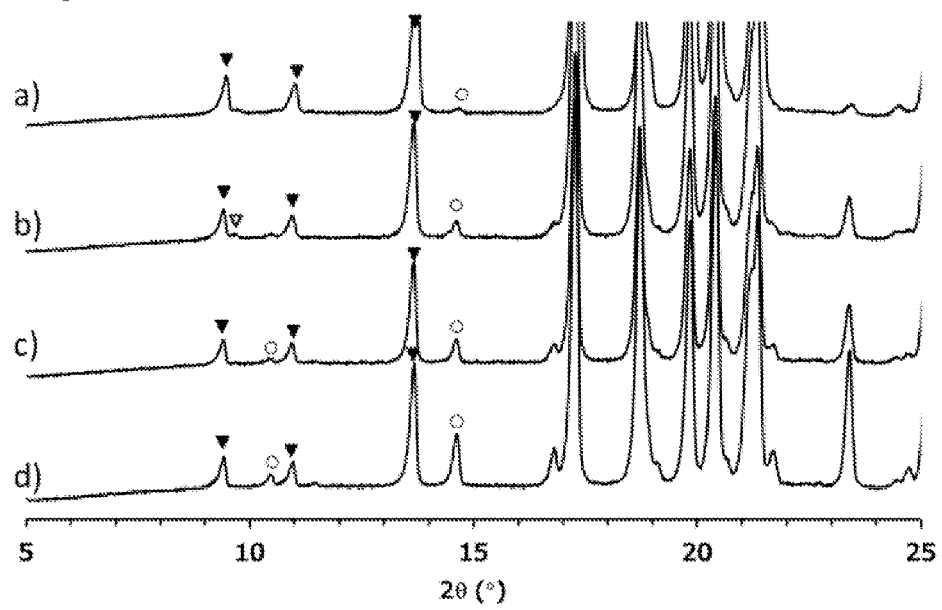
[Fig. 13]

[Fig. 14]
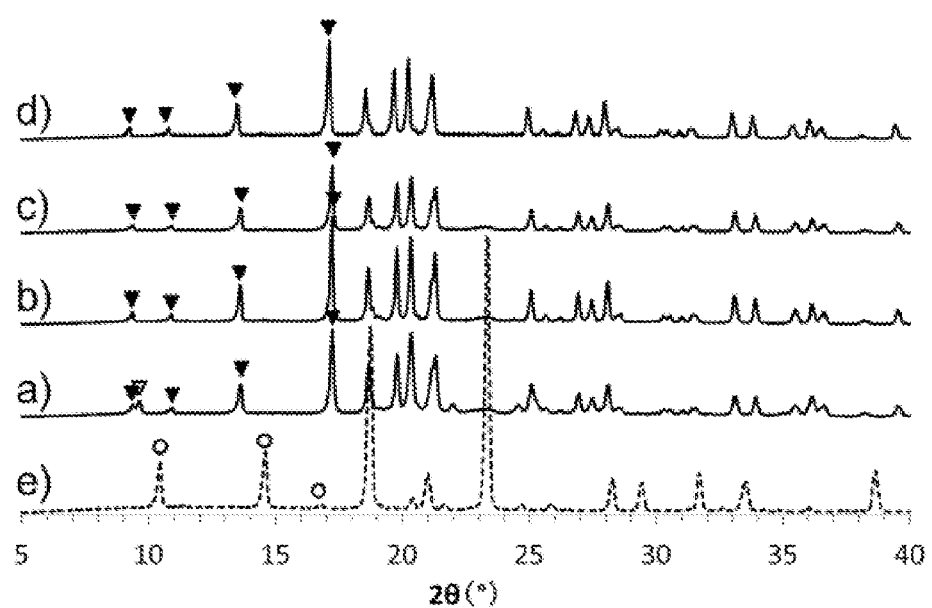

[Fig. 15]
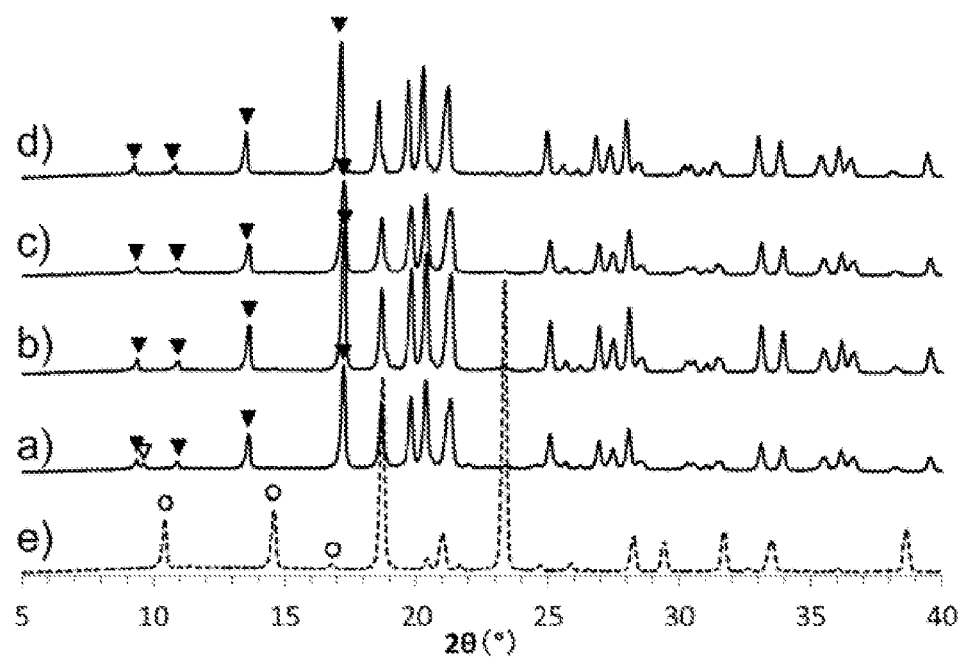

[Fig. 16]
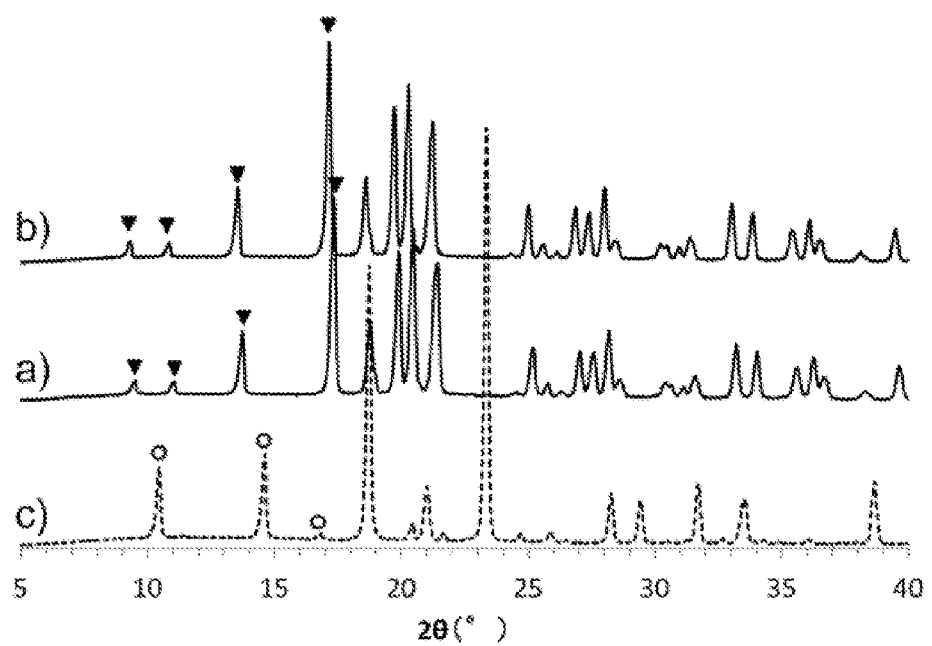

[Fig. 17]
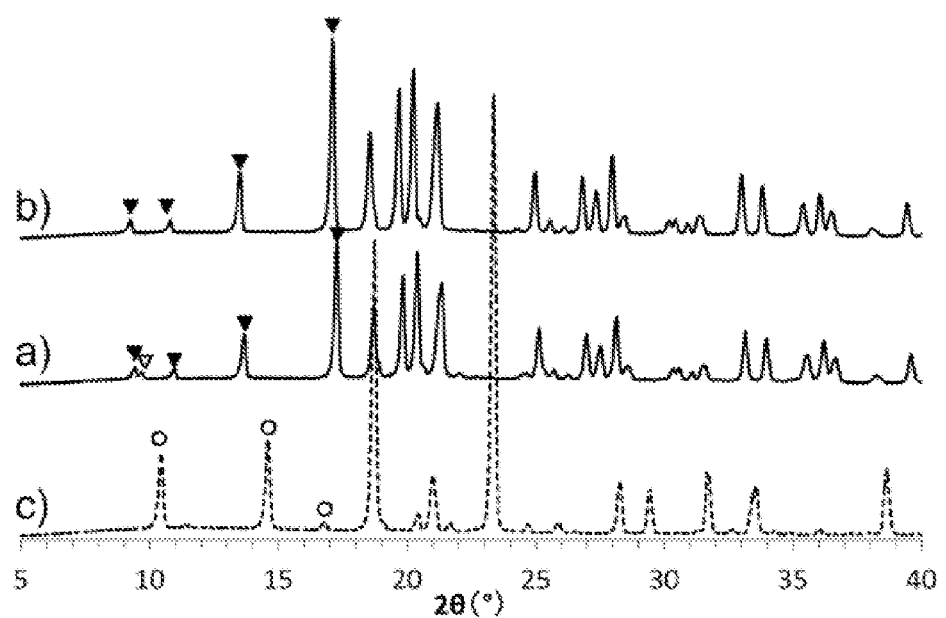

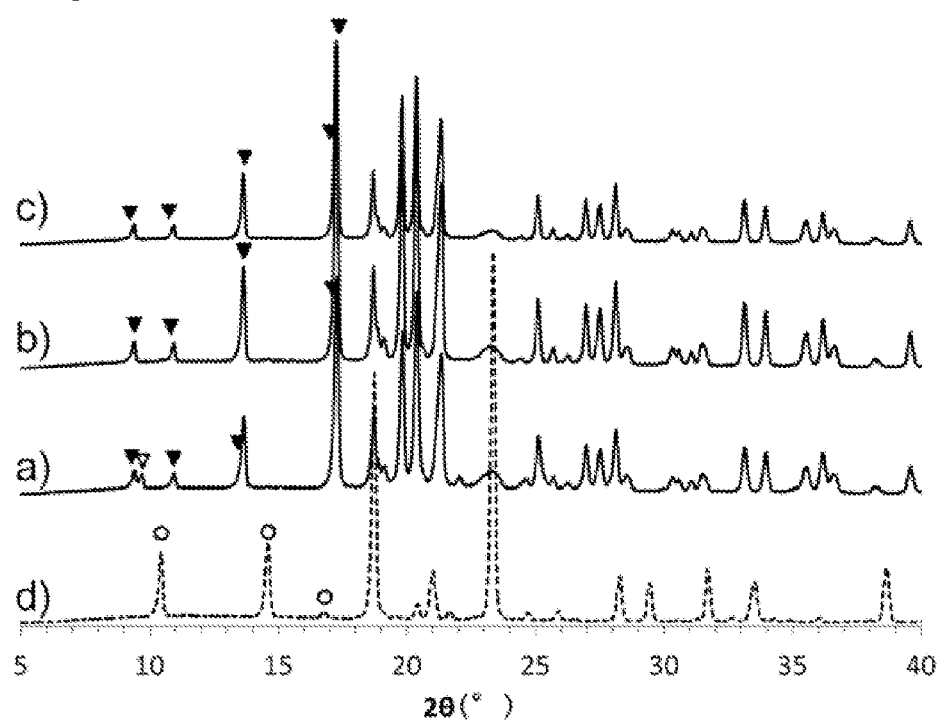
[Fig. 18]

[Fig. 19]
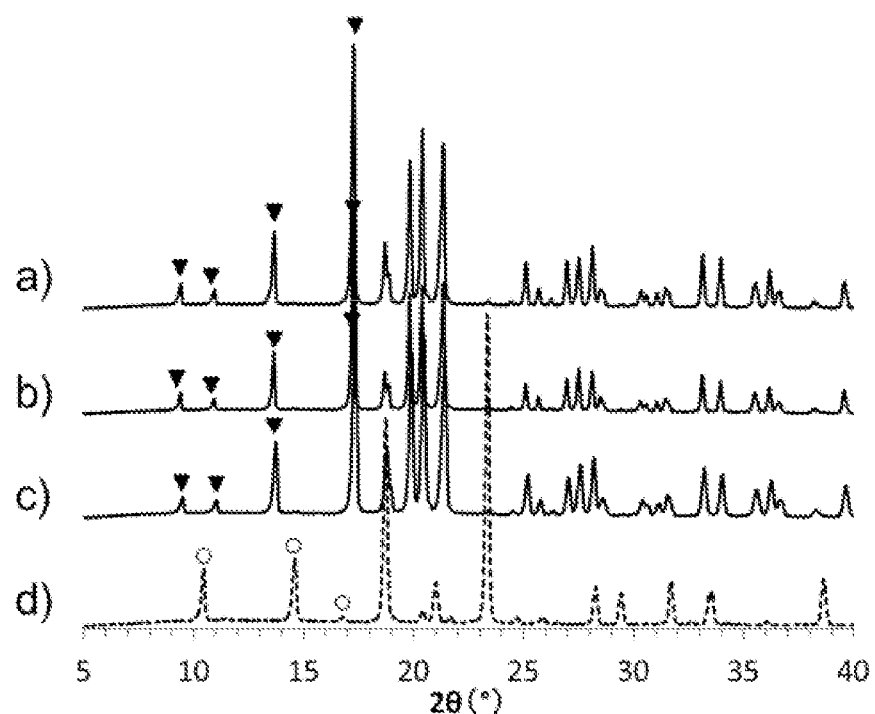

[Fig. 20]
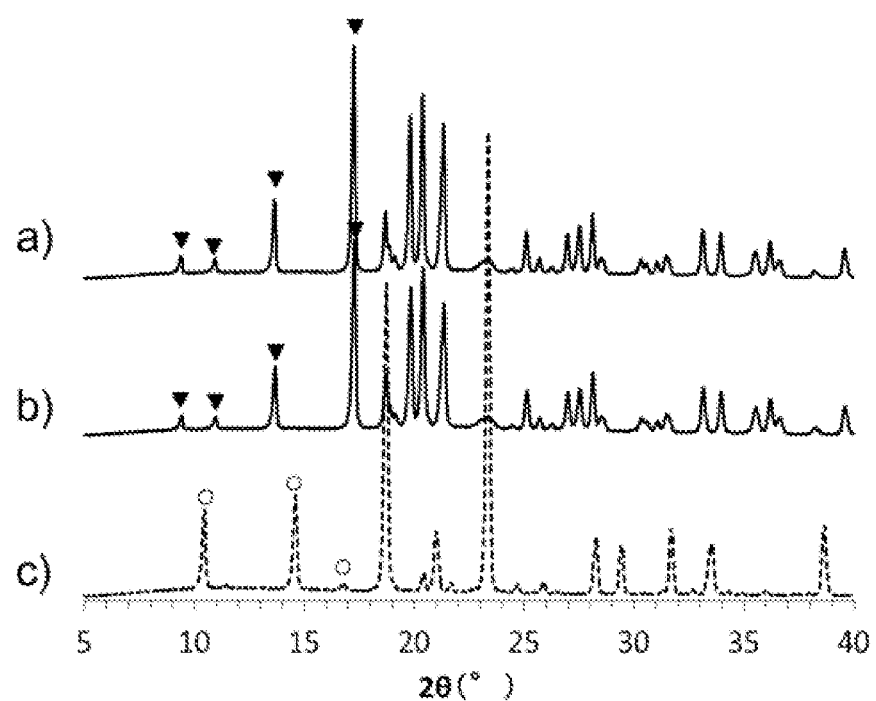

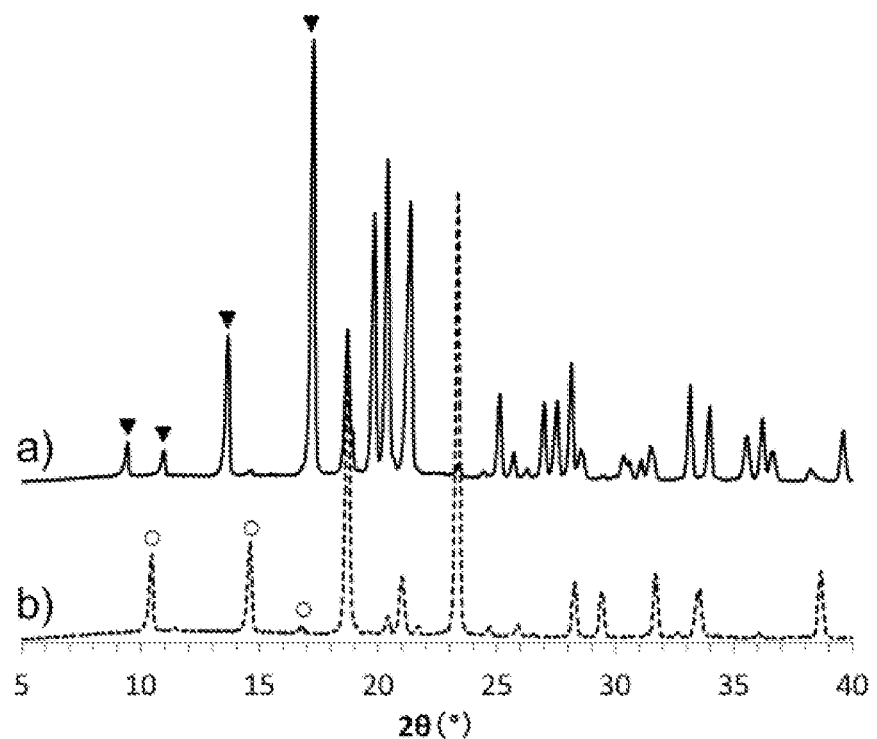
[Fig. 21]

[Fig. 22]
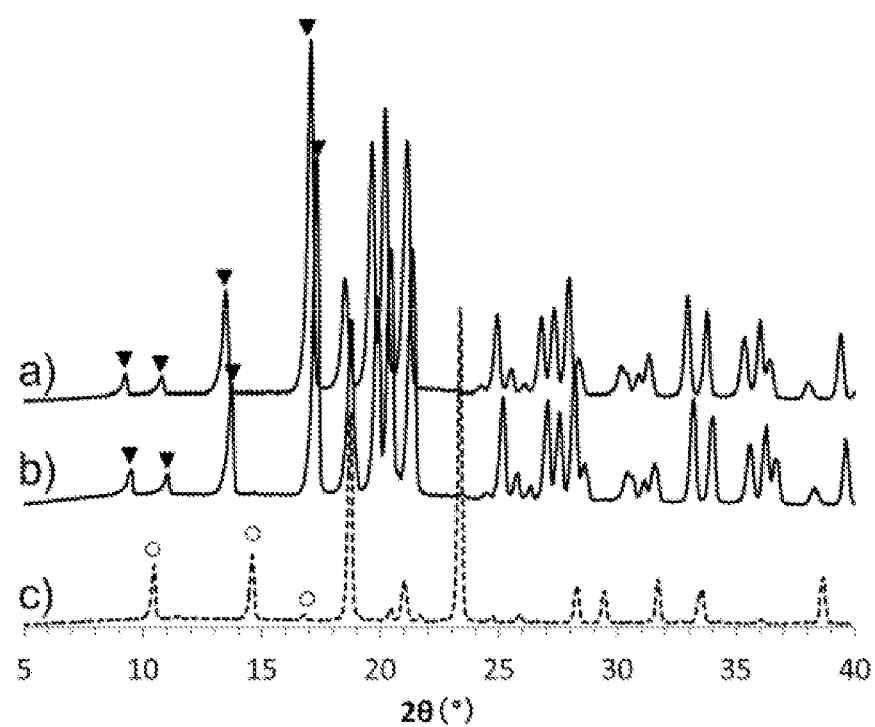

SELECTIVE PRODUCTION METHOD FOR D-MANNITOL α-FORM CRYSTAL USING SPRAY-DRYING METHOD

This application is a national phase entry under 35 U.S.C. § 371 of International Application Number PCT/JP2014/075815, filed Sep. 29, 2014, entitled "SELECTIVE PRODUCTION METHOD FOR D-MANNITOL α-FORM CRYSTAL USING SPRAY-DRYING METHOD", which claims the benefit of Japanese Patent Application Number 2013-202857, filed Sep. 30, 2013, all of which are hereby incorporated by reference in their entireties.

BACKGROUND OF THE INVENTION

Field of the Invention

The present invention relates to a method for producing selectively a powder particle comprising the α-form crystal of D-mannitol from a solution containing a water-soluble polymer such as polyethylene glycol (PEG) by using a spray dryer.

Background Art

The spray-drying method is one of the granulation methods, in which a spray dryer is used, and it is a method for drying a solution or a suspension of a pharmaceutical compound, a pharmaceutical additive, or their mixture, as fine liquid droplets, in a chamber within a short time by spraying from a nozzle with small hole diameter with hot air. It is known that powder particles with good fluidity can be obtained by the spray-drying method, and thus it is used as a method for producing not only powders of pharmaceuticals but also carrier particles prepared from inactive pharmaceutical additives such as lactose. The spray-drying method is widely known as a method for producing amorphous dry powder particles. In addition, it also receives attention from the viewpoint of producing particles with various shapes or different surface states and controlling physical properties of obtained particles such as crystal form depending on the solid content in the solution, spray speed, drying temperature, or the like. (see, Non Patent Literature 1, for example).

As a pharmaceutical dosage form in which pharmaceutical particles or carrier particles are used, dry powder inhalants (DPI) are known, for example. DPI is a dosage form to be inhaled as an aerosol of solid particles, which is produced to provide a constant inhalation amount. For solving problems such as adhesion and residuals, for most DPIs, the adhesion property is lowered so that inhalation can be promoted by having a secondary particle formed with an inactive carrier prepared from additives such as lactose. Presently, this is a well used formulation for an adrenocorticosteroidal agent for treating asthma. Furthermore, various inhalants including DPI have been conventionally employed for administration methods for having a local action and avoiding systemic adverse effects, but are also expected to be used as formulations for transpulmonary administration for possibly having a systemic action (see, Non Patent Literatures 2 and 3, for example).

Among the dry powder inhalants (DPI), lactose is known as an inactive carrier (diluent) that is generally used. There is a report in which α-lactose monohydrate is used for DPI (see, Patent Literature 1, for example).

Similar to lactose, D-mannitol as a sugar alcohol is widely used as a pharmaceutical additive. It is known that there are three crystal polymorphs of D-mannitol, that is, β-form (which may be also referred to as modification type I), α-form (which may be also referred to as modification type II), and δ-form (which may be also referred to as modification type III). Each of those three crystal polymorphs including β-form crystal as the most stable crystal, α-form crystal, and δ-form crystal as the most unstable crystal can be produced by a different crystallization method. Melting points and spectrum data such as powder X ray diffraction patterns are known for each of them. However, as commercially available (purchasable) D-mannitol crystals with a single crystal form, there are only the β-form crystal and the δ-form crystal (see, Non Patent Literature 4, for example).

Until now, studies have been made regarding production of crystal polymorphs based on modifications of process parameters such as the spray speed for the spray-drying method (see, Non Patent Literatures 5 and 6, for example).

DESCRIPTION OF RELATED ART

Patent Literature 1: JP 2007-509941 A

Non Patent Literatures

Non Patent Literature 1: The Pharmaceutical Society of Japan, "Explanations of Pharmaceutical Terminology", "Spray-Drying Method", [searched on Sep. 1, 2014], internet <URL: http://www.pharm.or.jp/dictionary/wiki.cgi?%e3%82%b9%e3%83%97%e3%83%ac%e3%83%bc%e3%83%89%e3%83%a9%e3%82%a4%e6%b3%95>

Non Patent Literature 2: The Pharmaceutical Society of Japan, "Explanations of Pharmaceutical Terminology", "Powder Inhaler", [searched on Sep. 1, 2014], internet <URL: http://www.pharm.or.jp/dictionary/wiki.cgi?%e7%b2%89%e6%9c%ab%e5%90%b8%e5%85%a5%e5%89%a4>

Non Patent Literature 3: Japanese Pharmacopoeia, $16^{th}$ Ed. (General Rules for Preparations) "5.1. Inhalations"

Non Patent Literature 4: A. Burger, et. al., Journal of Pharmaceutical Sciences, 2000, 89 (4), 457-468.

Non Patent Literature 5: E. M. Littringer, et. al., Drying Technology, 30: 114-124, 2012.

Non Patent Literature 6: Yan-Y. Lee, et. al., European Journal of Pharmaceutical Science, 44 (2011) 41-48.

BRIEF SUMMARY OF THE INVENTION

Until now, a method for obtaining selectively the α-form crystal of D-mannitol by the spray-drying method has not been known. Accordingly, an object of the present invention is to provide a method for obtaining the α-form crystal of D-mannitol by using the spray-drying method.

The inventors of the present invention conducted intensive studies to solve the aforementioned problems, and found that, by subjecting a solution containing a water-soluble polymer and D-mannitol to spray drying, the α-form crystal of D-mannitol can be selectively obtained. The present invention is completed accordingly.

Namely, the present invention relates to the following:

(1) A method for producing the α-form crystal of D-mannitol, including a step of performing spray drying of a solution containing D-mannitol and a water-soluble polymer;

(2) Particles containing the α-form crystal of D-mannitol and a water-soluble polymer;

(3) A method for producing selectively powder particles comprising the α-form crystal of D-mannitol, wherein a D-mannitol solution containing a water-soluble polymer is spray-dried; and (4) A method for producing powder particles containing the α-form crystal of D-mannitol and a water-soluble polymer comprising (i) a step of dissolving D-mannitol and a water-soluble polymer in a solvent and (ii) a step of subjecting the solution obtained from the step (i) to spray drying.

According to the present invention, powder particles comprising the α-form crystal of D-mannitol can be selectively produced.

BRIEF DESCRIPTION OF THE SEVERAL VIEWS OF THE DRAWINGS

FIG. 1 shows powder X ray diffraction patterns of β-form crystal of D-mannitol (pattern a), of the powder particles obtained by spray-drying an aqueous solution of D-mannitol (not containing a water-soluble polymer) (pattern b), and of α-form crystal of D-mannitol (pattern c). In the drawing, the filled triangles represent the characteristic diffraction peaks of the α-form crystal of D-mannitol, and the empty circles represent the characteristic diffraction peaks of the β-form crystal of D-mannitol.

FIG. 2 shows powder X ray diffraction patterns of β-form crystal of D-mannitol (pattern a), and of the powder particles obtained by spray-drying an aqueous solution of D-mannitol (not containing a water-soluble polymer) (pattern b), by spray-drying a 10% aqueous ethanol solution of D-mannitol (not containing a water-soluble polymer) (pattern c), or by spray-drying a 25% aqueous ethanol solution of D-mannitol (not containing a water-soluble polymer) (pattern d). In the drawing, the filled triangles and empty circles represent characteristic diffraction peaks of the α-form crystal of D-mannitol and characteristic diffraction peaks of the β-form crystal of D-mannitol, respectively.

FIG. 3 shows powder X ray diffraction patterns of β-form crystal of D-mannitol (pattern a), and of the powder particles obtained by spray-drying an aqueous solution of D-mannitol (not containing a water-soluble polymer) (pattern b), by spray-drying a 25% aqueous acetone solution of D-mannitol (not containing a water-soluble polymer) (pattern c), or by spray-drying a 50% aqueous acetone solution of D-mannitol (not containing a water-soluble polymer) (pattern d). In the drawing, the filled triangles and empty circles represent characteristic diffraction peaks of the α-form crystal of D-mannitol and characteristic diffraction peaks of the β-form crystal of D-mannitol, respectively.

FIG. 4 shows powder X ray diffraction patterns of the powder particles obtained from Comparative Example 1 (pattern a), or Examples 1 (pattern b), 2 (pattern c), 3 (pattern d), and 4 (pattern e). In the drawing, the filled triangles and empty circles represent characteristic diffraction peaks of the α-form crystal of D-mannitol and characteristic diffraction peaks of the β-form crystal of D-mannitol, respectively.

FIG. 5 shows powder X ray diffraction patterns of the powder particles obtained from Comparative Examples 2 (pattern a) and 3 (pattern b), and Examples 5 (pattern c) and 6 (pattern d). In the drawing, the filled triangles and empty circles represent characteristic diffraction peaks of the α-form crystal of D-mannitol and characteristic diffraction peaks of the β-form crystal of D-mannitol, respectively.

FIG. 6 shows powder X ray diffraction patterns of the powder particles obtained from Comparative Examples 4 (pattern a) and 5 (pattern b), and Examples 7 (pattern c) and 8 (pattern d). In the drawing, the filled triangles and empty circles represent characteristic diffraction peaks of the α-form crystal of D-mannitol and characteristic diffraction peaks from the β-form crystal of D-mannitol, respectively.

FIG. 7 shows powder X ray diffraction patterns of the powder particles obtained from Examples 9 (pattern a), 10 (pattern b), 11 (pattern c) and 12 (pattern d). In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 8 shows powder X ray diffraction patterns of the powder particles obtained from Examples 13 (pattern a), 14 (pattern b), 15 (pattern c) and 16 (pattern d). In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 9 shows powder X ray diffraction patterns of the powder particles obtained from Examples 17 (pattern a), 18 (pattern b), 19 (pattern c) and 20 (pattern d). In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 10 shows powder X ray diffraction patterns of the powder particles obtained from Examples 21 (pattern a), 22 (pattern b), 23 (pattern c), 24 (pattern d), 25 (pattern e), 26 (pattern f), 27 (pattern g) and 28 (pattern h). In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peak of the δ-form crystal of D-mannitol, respectively.

FIG. 11 shows powder X ray diffraction patterns of the powder particles obtained from Examples 29 (pattern a), 30 (pattern b), 31 (pattern c) and 32 (pattern d). In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 12 shows powder X ray diffraction patterns of the powder particles obtained from Examples 33 (pattern a) and 34 (pattern b). In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 13 shows powder X ray diffraction patterns of the powder particles obtained from Examples 35 (pattern a), 36 (pattern b), 37 (pattern c) and 38 (pattern d). In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 14 shows a powder X ray diffraction patterns of the powder particles obtained from Example 39. Pattern a is a powder X ray diffraction pattern right after production, pattern b is a powder X ray diffraction pattern after one-week storage, pattern c is a powder X ray diffraction pattern after four-week storage, and pattern d is a powder X ray diffraction pattern after three-month storage. Pattern e is a powder X ray diffraction pattern of the β-form crystal of D-mannitol. In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 15 shows powder X ray diffraction patterns of the powder particles obtained from Example 40. Pattern a is a powder X ray diffraction pattern right after production, pattern b is a powder X ray diffraction pattern after one-week storage, pattern c is a powder X ray diffraction pattern after four-week storage, and pattern d is a powder X ray diffraction pattern after three-month storage. Pattern e is a powder X ray diffraction pattern of the β-form crystal of D-mannitol. In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 16 shows powder X ray diffraction patterns of powder particles obtained from Example 41. Pattern a is a powder X ray diffraction pattern right after production and pattern b is a powder X ray diffraction pattern after three-month storage. Pattern c is a powder X ray diffraction pattern of the β-form crystal of D-mannitol. In the drawing, the filled triangles and empty circles represent characteristic diffraction peaks of the α-form crystal of D-mannitol and characteristic diffraction peaks of the β-form crystal of D-mannitol, respectively.

FIG. 17 shows powder X ray diffraction patterns of the powder particles obtained from Example 42. Pattern a is a powder X ray diffraction pattern right after production and pattern b is a powder X ray diffraction pattern after three-month storage. Pattern c is a powder X ray diffraction pattern of the β-form crystal of D-mannitol. In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 18 shows powder X ray diffraction patterns of the powder particles obtained from Example 43. Pattern a is a powder X ray diffraction pattern right after production, pattern b is a powder X ray diffraction pattern after one-month storage, and pattern c is a powder X ray diffraction pattern after six-month storage. Pattern d is a powder X ray diffraction pattern of the β-form crystal of D-mannitol. In the drawing, the filled triangles, empty circles, and empty triangles represent characteristic diffraction peaks of the α-form crystal of D-mannitol, characteristic diffraction peaks of the β-form crystal of D-mannitol, and characteristic diffraction peaks of the δ-form crystal of D-mannitol, respectively.

FIG. 19 shows powder X ray diffraction patterns of the powder particles obtained from Examples 44 (pattern a), 45 (pattern b) and 46 (pattern c). Pattern d is a powder X ray diffraction pattern of the β-form crystal of D-mannitol. In the drawing, the filled triangles and empty circles represent characteristic diffraction peaks of the α-form crystal of D-mannitol and characteristic diffraction peaks of the β-form crystal of D-mannitol, respectively.

FIG. 20 shows powder X ray diffraction patterns of the powder particles obtained from Examples 47 (pattern a) and 48 (pattern b). Pattern c is a powder X ray diffraction pattern of the β-form crystal of D-mannitol. In the drawing, the filled triangles and empty circles represent characteristic diffraction peaks of the α-form crystal of D-mannitol and characteristic diffraction peaks of the β-form crystal of D-mannitol, respectively.

FIG. 21 shows powder X ray diffraction patterns of the powder particles obtained from Example 49 (pattern a). Pattern b is a powder X ray diffraction pattern of the β-form crystal of D-mannitol. In the drawing, the filled triangles and empty circles represent characteristic diffraction peaks of the α-form crystal of D-mannitol and characteristic diffraction peaks of the β-form crystal of D-mannitol, respectively.

FIG. 22 shows powder X ray diffraction patterns of the powder particles obtained from Examples 50 (pattern a) and 51 (pattern b). Pattern c is a powder X ray diffraction pattern of the β-form crystal of D-mannitol. In the drawing, the filled triangles and empty circles represent characteristic diffraction peaks of the α-form crystal of D-mannitol and characteristic diffraction peaks of the β-form crystal of D-mannitol, respectively.

DETAILED DESCRIPTION OF THE INVENTION

The crystal form of D-mannitol used for the method of the present invention can be any one of the α form, β form and δ form. β-Form crystal and δ-form crystal D-mannitol can be purchased from Merck Millipore, for example. α-Form crystal D-mannitol can be produced by using the method described in Non Patent Literature 4.

Examples of the water-soluble polymer which can be used for the present invention include pectin, carboxyvinyl polymer, brown algae extract, locust bean gum, sodium alginate, hydroxyethyl cellulose, hydroxypropyl cellulose, hypromellose, methyl cellulose, sodium carboxy methylcellulose, xanthan gum, polyethylene oxide, polyethylene glycol (PEG), polyvinyl pyrrolidone (PVP), polyvinyl alcohol (PVA), and polyvinyl pyrrolidone vinylacetate (PVP-VA). It is preferably PEG, PVP, or PVA, and more preferably PEG.

As for the PEG, a commercially available product can be used. For example, PEG having a molecular weight per molar equivalent (molar weight) in the range of 190 g/mol to 25000 g/mol, which is commercially available as PEG 200 to 20000, can be used. The PEG used in the present invention is preferably PEG with a molecular weight in the range of 2600 g/mol to 3800 g/mol, which is commercially available as PEG 4000.

The solution used for the present invention is a mixture solution of a water-soluble organic solvent and water or an aqueous solution, and it is preferably an aqueous solution. Examples of the water-soluble organic solvent include a C1 to C6 alcohol-based solvent and a C3 to C5 ketone-based solvent.

As described herein, the "C1 to C6 alcohol-based solvent" means a monovalent C1 to C6 alkanol in which one hydrogen atom on a linear or branched saturated hydrocarbon with 1 to 6 carbon atoms is substituted by a hydroxyl group. Examples of the monovalent C1 to C6 alkanol include methanol, ethanol, n-propanol, 2-propanol, 1-butanol, 2-butanol, isobutyl alcohol, tert-butyl alcohol, 1-pentanol, 2-pentanol, 3-pentanol, 2-methyl-1-butanol, 3-methyl-1-butanol, 2-methyl-2-butanol, 3-methyl-2-butanol, 2-2-dimethyl-1-propanol, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2-2-dimethyl-1-butanol, 2-3-dimethyl-1-butanol, 3-3-dimethyl-1-butanol, 2-3-dimethyl-2-butanol, 3-3-dimethyl-2-butanol, and 2-ethyl-1-butanol. Of these, methanol, ethanol, n-propanol, or 2-propanol is preferable. Ethanol is more preferable.

As described herein, the "C3 to C5 ketone-based solvent" means a dialkyl ketone having 3 to 5 carbon atoms which is formed of a carbonyl carbon of a carbonyl group and two alkyl groups bonded to the carbonyl carbon. Examples thereof include acetone, ethyl methyl ketone, methyl propyl ketone, and diethyl ketone. Of these, acetone and ethyl methyl ketone are preferable, and acetone is more preferable.

The mixing ratio between the water-soluble organic solvent and water in the mixture solution used for the present invention is not particularly limited provided it is within the range allowing dissolution of D-mannitol and the water-soluble polymer. A preferred mixture solution of the water-soluble organic solvent and water is a 10 to 50% aqueous methanol solution, a 10 to 50% aqueous ethanol solution, or a 10 to 50% aqueous acetone solution.

The concentration of D-mannitol in the solution used for the present invention is not particularly limited, but it is preferably 1 to 20% (w/w), and more preferably 5 to 15% (w/w).

The concentration of the water-soluble polymer in the solution used for the present invention is not particularly limited, but it is preferably 1 part by weight or more, more preferably 2 parts by weight or more, still more preferably 5 parts by weight or more, and particularly preferably 10 parts by weight or more, per 100 parts by weight of D-mannitol. In other words, the ratio of the water-soluble polymer relative to D-mannitol is preferably 1% by weight or more, more preferably 2% by weight or more, even more preferably 5% by weight, and particularly preferably 10% by weight or more. The upper limit of the concentration of the water-soluble polymer in the solution used for the present invention is not particularly limited, but it is preferably 100 parts by weight or less, more preferably 80 parts by weight or less, and even more preferably 60 parts by weight or less, per 100 parts by weight of D-mannitol.

As described herein, the spray drying means a method of producing a dry powder by spraying and rapidly drying a solution or a suspension in gas. Spray drying can be performed by using a commercially available spray dryer.

The conditions for spray drying are not particularly limited, as they vary depending on the equipment or the like. However, if a GS-31 type spray dryer manufactured by Yamato Scientific Co., Ltd. is used, for example, it is possible that the spray air pressure is 0.5 to 2 kgf/cm$^2$, the liquid feeding speed is 0.5 to 10 g/min, and the inlet air temperature is 100 to 200° C.

EXAMPLES (Measurement of Powder X Ray Diffraction Pattern)

Powder X ray diffraction pattern was measured by using a powder X ray diffractometer Empyrean system (Panalytical B.V.). The measurement conditions were CuKα radiation, 40 kV voltage, 40 mA current over the 2θ range between 5 and 40°

(Materials)

As for the β-form crystal of D-mannitol, EMPROVE by Merck was used. PEG 4000 was purchased from Wako Pure Chemicals. PEG 400 was purchased from Kishida Chemical Co., Ltd. PVP was purchased from BASF Japan Ltd. PVA was purchased from Wako Pure Chemical Industries, Ltd.

Reference Example 1

Powder X ray diffraction pattern of the β-form crystal of D-mannitol was measured. The result is shown in FIG. 1 a).

An aqueous solution containing D-mannitol was prepared. The obtained solution was spray-dried under the following conditions.
(Spray Drying Conditions)
Equipment: GS-31 type spray dryer (Yamato Scientific Co., Ltd.)
Spray air pressure: 0.9 to 1.1 kgf/cm$^2$
Liquid feeding (spray) speed: about 3.0 g/min
Inlet air temperature: 124 to 127° C. (about 125° C.)
Powder X ray diffraction pattern of the obtained particle was measured, and the result is shown in FIG. 1 b).

D-Mannitol (α-form crystal) was prepared according to the method described in Non Patent Literature 4. Specifically, D-mannitol (β-form crystal) (10 g) was dissolved in 70% aqueous ethanol solution (90 g) and the solution was slowly cooled to 20° C. or lower. The solution was stored at 4° C. for 12 hours. The precipitated crystals were collected by filtration and dried at 40° C. to obtain D-mannitol (α-form crystal). Powder X ray diffraction pattern of the obtained D-mannitol was measured, and the pattern is shown in FIG. 1 c).

Reference Example 2

Powder X ray diffraction pattern of β-form crystal of D-mannitol was measured. The result is shown in FIG. 2 a).

An aqueous solution containing D-mannitol was prepared. The obtained solution was spray-dried under the same conditions as Reference Example 1. Powder X ray diffraction pattern of the obtained particles was measured, and the result is shown in FIG. 2 b).

10% Aqueous ethanol solution or 25% aqueous ethanol solution containing D-mannitol was prepared. The obtained solution was spray-dried under the same conditions as Reference Example 1. Powder X ray diffraction patterns of the obtained particles were measured, and the results are shown in FIGS. 2 c) and d), respectively.

It was found that, when spray drying is performed by using an aqueous ethanol solution, it is mostly the β-form crystal of D-mannitol even though co-presence of the α-form crystal of D-mannitol is observed.

Reference Example 3

Powder X ray diffraction pattern of β-form crystal of D-mannitol was measured. The result is shown in FIG. 3 a).

An aqueous solution containing D-mannitol was prepared. The obtained solution was spray-dried under the same conditions as Reference Example 1. Powder X ray diffraction pattern of the obtained particles was measured, and the result is shown in FIG. 3 b).

25% Aqueous acetone solution or 50% aqueous acetone solution containing D-mannitol was prepared. The obtained solution was spray-dried under the same conditions as Reference Example 1. Powder X ray diffraction patterns of the obtained particles were measured, and the results are shown in FIGS. 3 c) and d), respectively.

It was found that, when spray drying is performed by using an aqueous acetone solution, it is mostly the β-form crystal of D-mannitol even though co-presence of the α-form crystal of D-mannitol is observed.

Examples 1 to 4 and Comparative Example 1

A solution was prepared by dissolving 10 g of D-mannitol (β-form crystal) and 20 mg (Example 1), 50 mg (Example 2), 100 mg (Example 3) or 1 g (Example 4) of PEG 4000 in 190 g of purified water. The obtained solution was spray-dried under the same conditions as Reference Example 1. Powder X ray diffraction patterns of the obtained particles were measured, and the results are shown in FIGS. 4 *b*), *c*), *d*), and *e*), respectively.

A solution was prepared by dissolving 10 g of D-mannitol (β-form crystal) in 190 g of purified water (Comparative Example 1). The obtained solution was spray-dried under the same conditions as Reference Example 1. Powder X ray diffraction pattern of the obtained particle was measured, and the result is shown in FIG. 4 *a*).

TABLE 1

|  | Comparative Example 1 | Example 1 | Example 2 | Example 3 | Example 4 |
|---|---|---|---|---|---|
| D-mannitol (β-form crystal) | 10 g | 10 g | 10 g | 10 g | 10 g |
| PEG 4000 | 0 g | 20 mg | 50 mg | 100 mg | 1 g |
| Purified water | 190 g | 190 g | 190 g | 190 g | 190 g |
| PEG 4000 ratio (relative to D-mannitol w/w) | 0% | 0.2% | 0.5% | 1% | 10% |
| Crystal form of obtained powder | β | α + β | α + β | α | α |

It was found that the α-form crystal of D-mannitol can be produced by using PEG 4000. Furthermore, when the ratio of PEG 4000 is 1% or more relative to D-mannitol, it was possible to produce the α-form crystal of D-mannitol without co-presence of the β-form crystal of D-mannitol, that is, the α-form crystal of D-mannitol can be selectively produced.

Examples 5 and 6 and Comparative Examples 2 and 3

25% Aqueous acetone solution containing β-form crystal of D-mannitol and 1 w/w % (Example 5) or 10 w/w % (Example 6) PEG 4000 relative to D-mannitol was prepared. The obtained solution was spray-dried under the same conditions as Reference Example 1. Powder X ray diffraction patterns of the obtained particles were measured, and the results are shown in FIGS. 5 *c*) and *d*), respectively.

An aqueous solution (Comparative Example 2) or 25% aqueous acetone solution (Comparative Example 3) containing D-mannitol was prepared. The obtained solution was spray-dried under the same conditions as Reference Example 1. Powder X ray diffraction patterns of the obtained particles were measured, and the results are shown in FIGS. 5 *a*) and *b*), respectively.

It was found that, by using PEG 4000, the α-form crystal of D-mannitol can be produced without co-presence of the β-form crystal of D-mannitol, that is, the α-form crystal of D-mannitol can be selectively produced.

Examples 7 and 8 and Comparative Examples 4 and 5

25% Aqueous ethanol solution containing β-form crystal of D-mannitol and 1 w/w % PVP (Example 7) or 1 w/w % PVA (Example 8) relative to D-mannitol was prepared. The obtained solution was spray-dried under the same conditions as Reference Example 1. Powder X ray diffraction patterns of the obtained particles were measured, and the results are shown in FIGS. 6 *c*) and *d*), respectively.

An aqueous solution (Comparative Example 4) or 25% aqueous ethanol solution (Comparative Example 5) containing D-mannitol was prepared. The obtained solution was spray-dried under the same conditions as Reference Example 1. Powder X ray diffraction patterns of the obtained particles were measured, and the results are shown in FIGS. 6 *a*) and *b*), respectively.

It was found that, by using a water-soluble polymer, the α-form crystal of D-mannitol can be produced without co-presence of the β-form crystal of D-mannitol, that is, the α-form crystal can be selectively produced.

Examples 9 to 38

Solutions having the compositions described in Table 2 to Table 9 were prepared. The obtained solutions were spray-dried according to the conditions described in Table 2 to Table 9. Powder X ray diffraction patterns of the obtained particles were measured, and the results are shown in FIG. 7 (Examples 9 to 12), 8 (Examples 13 to 16), 9 (Examples 17 to 20), 10 (Examples 21 to 28), 11 (Examples 29 to 32), 12 (Examples 33 to 34), and 13 (Examples 35 to 38).

TABLE 2

Influence of inlet air temperature (part 1)

|  | Example 9 | Example 10 | Example 11 | Example 12 |
|---|---|---|---|---|
| D-mannitol (β-form crystal) (%) | 15 | 15 | 15 | 15 |
| PEG 400 (%) | 0.15 | 0.15 | 0.075 | 0.075 |
| Purified water | balance | balance | balance | balance |
| Total (%) | 100 | 100 | 100 | 100 |
| PEG/D-mannitol (%) | 1 | 1 | 0.5 | 0.5 |
| Equipment | GS-31 type spray dryer (Yamato Scientific Co., Ltd.) | | | |
| Spray air pressure (kgf/cm$^2$) | 0.9 to 1.1 | | | |
| Liquid feeding speed (g/min) | about 3.0 | | | |
| Inlet air temperature (° C.) | about 150 | about 130 | about 150 | about 130 |

TABLE 3

Influence of inlet air temperature (part 2)

|  | Example 13 | Example 14 | Example 15 | Example 16 |
|---|---|---|---|---|
| D-mannitol (β-form crystal) (%) | 5 | 5 | 5 | 5 |
| PEG 4000 (%) | 0.05 | 0.05 | 0.025 | 0.025 |
| Purified water | balance | balance | balance | balance |
| Total (%) | 100 | 100 | 100 | 100 |
| PEG/D-mannitol (%) | 1 | 1 | 0.5 | 0.5 |
| Equipment | GS-31 type spray dryer (Yamato Scientific Co., Ltd.) | | | |

TABLE 3-continued

Influence of inlet air temperature (part 2)

|  | Example 13 | Example 14 | Example 15 | Example 16 |
|---|---|---|---|---|
| Spray air pressure (kgf/cm²) | 0.9 to 1.1 | | | |
| Liquid feeding speed (g/min) | about 3.0 | | | |
| Inlet air temperature (° C.) | about 150 | about 130 | about 150 | about 130 |

TABLE 4

Influence of D-mannitol concentration

|  | Example 17 | Example 18 | Example 19 | Example 20 |
|---|---|---|---|---|
| D-mannitol (β-form crystal) (%) | 15 | 5 | 15 | 5 |
| PEG 4000 (%) | 0.15 | 0.05 | 0.075 | 0.025 |
| Purified water | balance | balance | balance | balance |
| Total (%) | 100 | 100 | 100 | 100 |
| PEG/D-mannitol (%) | 1 | 1 | 0.5 | 0.5 |
| Equipment | GS-31 type spray dryer (Yamato Scientific Co., Ltd.) | | | |
| Spray air pressure (kgf/cm²) | 0.9 to 1.1 | | | |
| Liquid feeding speed (g/min) | about 3.0 | | | |
| Inlet air temperature (° C.) | about 130 | | | |

TABLE 5

Influence of PEG concentration (part 1)

|  | Example 21 | Example 22 | Example 27 | Example 28 |
|---|---|---|---|---|
| D-mannitol (β-form crystal) (%) | 5 | 5 | 5 | 5 |
| PEG 400 (%) | — | — | 0.1 | 0.05 |
| PEG 20000 (%) | 0.1 | 0.05 | — | — |
| Purified water | balance | balance | balance | balance |
| Total (%) | 100 | 100 | 100 | 100 |
| PEG/D-mannitol (%) | 2 | 1 | 2 | 1 |
| Equipment | GS-31 type spray dryer (Yamato Scientific Co., Ltd.) | | | |
| Spray air pressure (kgf/cm²) | 0.9 to 1.1 | | | |
| Liquid feeding speed (g/min) | about 3.0 | | | |
| Inlet air temperature (° C.) | about 130 | | | |

TABLE 6

Influence of PEG concentration (part 2)

|  | Example 23 | Example 24 | Example 25 | Example 26 |
|---|---|---|---|---|
| D-mannitol (β-form crystal) (%) | 5 | 5 | 5 | 5 |
| PEG 4000 (%) | 0.25 | 0.1 | 0.05 | 0.025 |
| Purified water | balance | balance | balance | balance |
| Total (%) | 100 | 100 | 100 | 100 |
| PEG/D-mannitol (%) | 5 | 2 | 1 | 0.5 |
| Equipment | GS-31 type spray dryer (Yamato Scientific Co., Ltd.) | | | |
| Spray air pressure (kgf/cm²) | 0.9 to 1.1 | | | |
| Liquid feeding speed (g/min) | about 3.0 | | | |
| Inlet air temperature (° C.) | about 130 | | | |

TABLE 7

Influence of molecular weight of PEG

|  | Example 29 | Example 30 | Example 31 | Example 32 |
|---|---|---|---|---|
| D-mannitol (β-form crystal) (%) | 5 | 5 | 5 | 5 |
| PEG 200 (%) | — | — | — | 0.05 |
| PEG 400 (%) | — | — | 0.05 | — |
| PEG 4000 (%) | — | 0.05 | — | — |
| PEG 20000 (%) | 0.05 | — | — | — |
| Purified water | balance | balance | balance | balance |
| Total (%) | 100 | 100 | 100 | 100 |
| PEG/D-mannitol (%) | 1 | 1 | 1 | 1 |
| Equipment | GS-31 type spray dryer (Yamato Scientific Co., Ltd.) | | | |
| Spray air pressure (kgf/cm²) | 0.9 to 1.1 | | | |
| Liquid feeding speed (g/min) | about 3.0 | | | |
| Inlet air temperature (° C.) | about 130 | | | |

TABLE 8

Influence of liquid feeding speed (part 1)

|  | Example 33 | Example 34 |
|---|---|---|
| D-mannitol (β-form crystal) (%) | 5 | 5 |
| PEG 400 (%) | 0.05 | 0.05 |
| Purified water | balance | balance |
| Total (%) | 100 | 100 |
| PEG/D-mannitol (%) | 1 | 1 |
| Equipment | GS-31 type spray dryer (Yamato Scientific Co., Ltd.) | |
| Spray air pressure (kgf/cm²) | 0.9 to 1.1 | |
| Liquid feeding speed (g/min) | about 1.5 | about 3.0 |
| Inlet air temperature (° C.) | about 130 | |

TABLE 9

Influence of liquid feeding speed (part 2)

|  | Example 35 | Example 36 | Example 37 | Example 38 |
|---|---|---|---|---|
| D-mannitol (β-form crystal) (%) | 5 | 5 | 5 | 5 |
| PEG 4000 (%) | 0.05 | 0.05 | 0.025 | 0.025 |
| Purified water | balance | balance | balance | balance |
| Total (%) | 100 | 100 | 100 | 100 |
| PEG/D-mannitol (%) | 1 | 1 | 0.5 | 0.5 |
| Equipment | GS-31 type spray dryer (Yamato Scientific Co., Ltd.) | | | |
| Spray air pressure (kgf/cm$^2$) | 0.9 to 1.1 | | | |
| Liquid feeding speed (g/min) | about 1.5 | about 3.0 | about 1.5 | about 3.0 |
| Inlet air temperature (° C.) | about 130 | | | |

It was found that, under wide condition ranges of inlet air temperature, D-mannitol concentration, PEG concentration, PEG molecular weight, and liquid feeding speed, the α-form crystal of D-mannitol can be produced by using PEG.

Examples 39 to 43

Solutions having the compositions described in Table 10 were prepared. The obtained solutions were spray-dried according to the conditions described in Table 10. Powder X ray diffraction patterns of the obtained particles were measured.

TABLE 10

|  | Example 39 | Example 40 | Example 41 | Example 42 | Example 43 |
|---|---|---|---|---|---|
| D-mannitol (β-form crystal) (%) | 5 | 5 | 15 | 15 | 5 |
| PEG 4000 (%) | 0.25 | 0.1 | — | — | 0.5 |
| PEG 400 (%) | — | — | 0.15 | 0.3 | — |
| Purified water | balance | balance | balance | balance | balance |
| Total (%) | 100 | 100 | 100 | 100 | 100 |
| PEG/D-mannitol (%) | 5 | 2 | 1 | 2 | 10 |
| Equipment | GS-31 type spray dryer (Yamato Scientific Co., Ltd.) | | | | |
| Spray air pressure (kgf/cm$^2$) | 0.9 to 1.1 | | | | |
| Liquid feeding speed (g/min) | about 3.0 | | | | |
| Inlet air temperature (° C.) | about 130 | about 130 | about 150 | about 130 | about 125 |

The particles obtained from above were stored at 40° C.±2° C. and 75% RH±5% RH, and changes in the powder X ray diffraction patterns were confirmed. The results are shown in FIG. 14 (Example 39), 15 (Example 40), 16 (Example 41), 17 (Example 42), and FIG. 18 (Example 43).

It is found that the α-form crystal of D-mannitol obtained from Examples 39 to 43 is hardly converted into the β-form crystal.

Examples 44 to 48

Solutions having compositions described in Table 11 were prepared. The obtained solutions were spray-dried according to the conditions described in Table 11. Powder X ray diffraction patterns of the obtained particles were measured. The results are shown in FIG. 19 (Examples 44 to 46) and FIG. 20 (Examples 47 and 48).

TABLE 11

|  | Example 44 | Example 45 | Example 46 | Example 47 | Example 48 |
|---|---|---|---|---|---|
| D-mannitol (β-form crystal) (%) | 5 | 5 | 5 | 5 | 5 |
| PEG 4000 (%) | 0.05 | 0.05 | 0.05 | 0.5 | 0.5 |
| Purified water (%) | balance | balance | balance | balance | balance |
| Total (%) | 100 | 100 | 100 | 100 | 100 |
| PEG/D-mannitol (%) | 1 | 1 | 1 | 10 | 10 |
| Equipment | B-290 type spray dryer (BUCHI Labortechnik AG) | | | | |
| Spray air pressure (kgf/cm$^2$) | 0.9 to 1.1 | | | | |
| Liquid feeding speed (g/min) | about 3.0 | | | | |
| Inlet air temperature (° C.) | about 200 | about 180 | about 160 | about 130 | about 130 |
| Exhaust air temperature (° C.) | 80 to 96 | 95 to 96 | 87 to 88 | 86 to 89 | 78 to 80 |

It is found that, even when different equipment is used, the α-form crystal of D-mannitol can still be manufactured by using PEG.

Examples 49 to 51

Solutions having the compositions described in Table 12 were prepared. The obtained solutions were spray-dried according to the conditions described in Table 12. Powder X ray diffraction patterns of the obtained particles were measured. The results are shown in FIG. 21 (Example 49) and FIG. 22 (Examples 50 and 51).

TABLE 12

|  | Example 49 | Example 50 | Example 51 |
|---|---|---|---|
| D-mannitol (β-form crystal) (%) | 5 | 5 | 5 |
| PEG 4000 (%) | 0.05 | — | 0.05 |
| PEG 400 (%) | — | 0.05 | — |
| Purified water (%) | balance | balance | balance |
| Total (%) | 100 | 100 | 100 |
| PEG/D-mannitol (%) | 1 | 1 | 1 |
| Equipment | CL-8i type spray dryer (OHKAWARA KAKOHKI CO., LTD.) | | |
| Revolution number of atomizer (rpm) | 40000 | | |
| Liquid feeding speed (g/min) | about 40 | | |
| Inlet air temperature (° C.) | about 140 | about 160 | about 160 |
| Exhaust air temperature (° C.) | 81 to 102 | 91 to 96 | 91 to 102 |

It is found that, even when different equipment is used, the α-form crystal of D-mannitol can still be manufactured by using PEG.

INDUSTRIAL APPLICABILITY

According to the present invention, the α-form crystal of D-mannitol can be selectively produced. The powder particles containing the α-form crystal of D-mannitol can be used as new carrier particles or the like of a pharmaceutical product.

The invention claimed is:

1. A method for producing selectively an α-form crystal of D-mannitol, comprising a step of performing spray drying of a solution consisting essentially of D-mannitol and a water-soluble polymer, wherein the solution is a mixture solution of a water-soluble organic solvent and water or an aqueous solution, wherein the water-soluble polymer is pectin, carboxyvinyl polymer, brown algae extract, locust bean gum, sodium alginate, hydroxyethyl cellulose, hydroxypropyl cellulose, hypromellose, methyl cellulose, sodium carboxy methylcellulose, xanthan gum, polyethylene oxide, polyethylene glycol, polyvinyl pyrrolidone, polyvinyl alcohol, or polyvinyl pyrrolidone vinylacetate, wherein the content of the water-soluble polymer in the solution is 1% to 60% by weight with respect to D-mannitol.

2. The method according to claim 1, wherein the water-soluble organic solvent is a C1 to C6 alcohol-based solvent or a C3 to C5 ketone-based solvent.

3. The method according to claim 1, wherein the water-soluble polymer is polyethylene glycol, polyvinyl pyrrolidone, or polyvinyl alcohol.

4. The method according to claim 1, wherein the water-soluble polymer is polyethylene glycol.

5. The method according to claim 1, wherein the molecular weight of the water-soluble polymer is 190 g/mol to 25000 g/mol.

6. The method according to claim 1, wherein the water-soluble polymer is polyethylene glycol 4000.

7. The method according to claim 1, wherein the content of the water-soluble polymer in the solution is 2% by weight or more with respect to D-mannitol.

8. The method according to claim 1, wherein the content of the water-soluble polymer in the solution is 5% by weight or more with respect to D-mannitol.

9. The method according to claim 1, wherein the content of the water-soluble polymer in the solution is 10% by weight or more with respect to D-mannitol.

* * * * *